United States Patent
Tolle

(10) Patent No.: US 10,806,659 B2
(45) Date of Patent: Oct. 20, 2020

(54) EYE EXERCISE DEVICE

(71) Applicant: Stephen Tolle, Marayong (AU)

(72) Inventor: Stephen Tolle, Marayong (AU)

(73) Assignee: Stephen Tolle, Marayong, NSW (AU)

(*) Notice: Subject to any disclaimer, the term of this patent is extended or adjusted under 35 U.S.C. 154(b) by 83 days.

(21) Appl. No.: 16/168,838

(22) Filed: Oct. 24, 2018

(65) Prior Publication Data

US 2019/0209419 A1   Jul. 11, 2019

(30) Foreign Application Priority Data

Jan. 7, 2018  (AU) ............................ 2018900041

(51) Int. Cl.
*A61H 5/00* (2006.01)
*A61B 3/08* (2006.01)
*A61B 3/00* (2006.01)

(52) U.S. Cl.
CPC ............ *A61H 5/00* (2013.01); *A61B 3/005* (2013.01); *A61B 3/08* (2013.01); *A61B 3/0008* (2013.01); *A61H 2201/165* (2013.01); *A61H 2201/5007* (2013.01)

(58) Field of Classification Search
CPC .......... A61H 5/00; A61H 2205/024; A61H 2201/1604; A61H 2201/1607; A61B 3/005; A61B 3/0008
See application file for complete search history.

(56) References Cited

U.S. PATENT DOCUMENTS

| | | | | |
|---|---|---|---|---|
| 4,756,305 A | * | 7/1988 | Mateik | A61B 3/08 601/37 |
| 5,308,246 A | * | 5/1994 | Balocco | A61B 5/16 434/236 |
| 5,737,060 A | * | 4/1998 | Kasha, Jr. | A61B 3/005 351/224 |
| 8,668,334 B2 | * | 3/2014 | Krenik | A61B 3/032 351/205 |
| 8,888,282 B2 | * | 11/2014 | Hong | G02C 7/083 351/159.39 |

(Continued)

FOREIGN PATENT DOCUMENTS

DE  202011050692 U1 * 9/2011 .......... A61N 5/0618
JP      11056942 A  * 3/1999

(Continued)

*Primary Examiner* — John Villecco

(57) ABSTRACT

An eye exercise device comprising a single open goggle chamber with no binocular or magnified optical lens of any sort having a front portion, protective first plate and second plate, light emitting diodes (LEDs), a control panel and a power supply, is disclosed. The control panel is coupled to the power supply, smart electronic glass and LEDs. The first plate is disposed at the front portion of the single open goggle chamber and the second plate is disposed behind the first plate. The second plate comprises a smart electronic glass and the first plate comprises a polycarbonate protective screen, disposed at a center region across an eye of a user. The smart electronic glass is configured to switch to an opaque state for short-sightedness and switch to a transparent state for farsightedness. The LEDs disposed at the periphery of the second plate is configured to emit light in a predefined sequence, thereby encouraging specific ocular movements.

8 Claims, 8 Drawing Sheets

(56) References Cited

U.S. PATENT DOCUMENTS

| | | | |
|---|---|---|---|
| 9,186,293 B2 * | 11/2015 | Krenik | A61B 3/032 |
| 10,179,081 B2 * | 1/2019 | Krenik | A61B 3/032 |
| 2001/0050754 A1 * | 12/2001 | Hay | G02C 7/101 |
| | | | 351/213 |
| 2005/0213034 A1 * | 9/2005 | Nagayoshi | A61H 5/00 |
| | | | 351/203 |
| 2007/0038142 A1 * | 2/2007 | Todd | G02B 27/0172 |
| | | | 600/558 |
| 2007/0200927 A1 * | 8/2007 | Krenik | A61B 3/036 |
| | | | 348/47 |
| 2008/0088936 A1 * | 4/2008 | Tang | G02B 27/0172 |
| | | | 359/630 |
| 2012/0123306 A1 * | 5/2012 | Pandozy | A61H 5/00 |
| | | | 601/37 |
| 2013/0342808 A1 * | 12/2013 | Hong | G02C 7/101 |
| | | | 351/159.56 |
| 2014/0192316 A1 * | 7/2014 | Krenik | A61H 23/02 |
| | | | 351/203 |
| 2014/0336723 A1 * | 11/2014 | Ben-Ezra | A61N 1/36025 |
| | | | 607/45 |
| 2016/0045388 A1 * | 2/2016 | Krenik | A61B 3/032 |
| | | | 351/201 |
| 2017/0296420 A1 * | 10/2017 | Ahn | A61F 9/029 |
| 2017/0322422 A1 * | 11/2017 | Stone | G02B 27/027 |
| 2018/0092796 A1 * | 4/2018 | Park | G02B 7/02 |
| 2019/0290528 A1 * | 9/2019 | Sgambelluri | A61H 5/00 |
| 2020/0008666 A1 * | 1/2020 | Anton Garcia | A61B 3/12 |
| 2020/0049992 A1 * | 2/2020 | Peng | G02B 5/3025 |
| 2020/0122015 A1 * | 4/2020 | Mast | A63B 71/0622 |

FOREIGN PATENT DOCUMENTS

| | | | | |
|---|---|---|---|---|
| JP | 2009089901 A | * | 4/2009 | |
| WO | WO-0210842 A1 | * | 2/2002 | G02C 7/165 |
| WO | WO-2009109111 A1 | * | 9/2009 | A61H 5/00 |

* cited by examiner

EYE EXERCISE DEVICE

CROSS REFERENCE TO RELATED APPLICATION

The present application claims the benefit of Australian Provisional Patent Application Number 2018900041 for "EYE EXERCISE DEVICE", filed Jan. 7, 2018, the contents of which is hereby incorporated by reference

BACKGROUND

A. Technical Field

The present invention generally relates to an eye exercise device. More specifically, the present invention relates to an eye exercise device without utilizing binocular lens & comprises of a single open goggle chamber with no binocular/magnified lens supporting the eye, protective first plate comprising a protective screen and second plate comprising an electronic smart glass or screen, light emitting diodes (LEDs), a control panel and a power supply. The control panel is coupled to the power supply, smart electronic glass and LEDs. The first plastic plate is disposed at the front portion of the single open goggle chamber and the second plastic plate is disposed behind the first plate. The second plate comprises a smart electronic glass and the first plate comprises a polycarbonate protective screen, disposed at a center region across an eye of a user. The smart electronic glass is configured to switch to an opaque state for short-sightedness and switch to a transparent state for farsightedness. The LEDs disposed at the periphery of the second plastic plate is configured to emit light in a predefined sequence, thereby encouraging specific ocular movements to rejuvenate the eye and strengthen the eye ocular muscles to provide short & long term benefit to the user.

B. Description of Related Art

Vision is the primary navigational system of a human body, which provides 80 to 95% information during a person's lifetime. The proficiency of the vision skill affects every human activity and human performance on all levels. However, the human vision system functions in a more and more difficult environment as educational and occupational demands continue to grow exponentially in today's society. Today's economy has entered an information age from industrial and service era. Hence, computers have become a common denominator for providing services and information in today's workforce. This leads to an explosive growth in screen use i.e., computers, smartphones, iPad, Tv's. An average American looks at a screen for over 9-10 hours per day (more time than sleeping hours), which dramatically increases vision problems including, but not limited to, eye fatigue and eye strain, strabismus, myopia, and hyperopia. Other factors like pollution, overuse of corrective lenses, blue light emitted from screens and incorrect eyeglasses also causes vision problems. The only solution offered by optometrists is a manual activity carried out by the individual where no assistance is provided and the person needs to remember manual exercises, which generally most of the population do not even know about in today's society. Few prior art references developed to address above problems is disclosed as follows & there are no prior art references that covers all of the ocular exercise naturally without any binocular/magnified supporting lenses in one x open chamber:

DE19905145 discloses a device for the stimulation of eye movements of a user. This device enables the stimulation of eye movements with large amplitude, the field of view under a horizontal angle of at least 80 degrees. The optical display elements are provided with LED's and control module for controlling the LEDs.

DE102011051741 discloses a device for light stimulation of biological tissue, particularly in the form of a device for the eye region of a user for exercising eye muscles. Based on exercising eye muscles the blue LED are respectively activated for a certain time. LED's designed as substantially circular, oval or arranged in the form of a polygon, wherein the first bulbs are blue LEDs. It is applicable for issues such as hyperopia (farsightedness), myopia (nearsightedness), asthenopia (visual impairment), presbyopia (presbyopia) etc. The movement of the eyes is performed by the external eye muscles. The outer eye muscles can be relaxed through exercises.

U.S. Pat. No. 8,317,320 discloses a spectacle frame, and more specially relates to a spectacle frame that is designed for multiple vision training of eyeball-moving and is able to effectively overcome asthenopia and control myopia. The frame, nose bridge and spectacle legs are provided with LED illuminant bodies. This invention effectively combines multi-vision training and 3-color ball training with the spectacle frame and can be used to train eyeballs to move toward different directions, thus fully exercising eye muscle. The spectacle frame enables wearers to make the exercise of eyeball movement whenever and wherever possible and really achieve the goal of overcoming asthenopia, improving eyesight and visual quality and controlling myopia.

Even though, the existing device provides eye exercise, certain critical exercises are not provided due to lack of modern design and technology. The design of these known devices is complex and expensive to manufacture to have excisable for the everyday household. The known devices could not facilitate the user to perform same exercise for both eyes and requires binocular lenses.

A prior art product, Izon is used for exercising eyes. This device comprises 2 chambers and binocular lenses with 2× shutters. Izon device accomplishes all of the eye exercises such as near sightedness, farsightedness with binocular lenses. The device uses 2× individual chambers, one for each eye and has a manual shutter that opens and closes to cater for near sightedness and farsightedness. However, this device also requires binocular lenses & the technology is out dated by approximately 14-15 years. The eye's cannot exercise at full ocular muscle stretch naturally.

Therefore, there is need for an eye exercise device utilizing a smart electronic glass in conjunction with a plurality of light emitting elements to encourage ocular muscle movements. Further, there is need for an eye exercise device that provides all types of exercise such as circular motion, crisscross motion, nearsightedness and farsightedness motion. Further, there is need for an eye exercise device that provides all types of ocular exercises without the use of binocular lenses. Also, binocular lenses might seem like a small thing but it is very difficult to achieve in a single open chamber without binocular lenses, which is key for the eyes to exercise naturally. Further, there is also a need to provide a new eye exercise device with a single open chamber without binocular lenses to facilitate the user to perform the same exercise for both eyes so they can fully stretch the ocular muscle without the support of assisted magnified/binocular lenses.

SUMMARY OF THE INVENTION

The present invention discloses an eye exercise device comprising a single open goggle chamber with no binocular/ magnified lenses. In one embodiment, the single open goggle chamber at the front portion, consists of at least two plates or holders such as a first plate and a second plate, a plurality of light emitting elements, and a control panel. In one embodiment, the first plate is disposed at the front portion of the single open goggle chamber. The first plate comprises a polycarbonate screen disposed at a center region across both eyes of a user.

In one embodiment, the second plastic plate is disposed behind the first plastic plate at the front portion. The second plastic plate comprises of a smart electronic glass or screen, disposed at a center region across both eyes of a user.

In one embodiment, the plurality light emitting elements is a light emitting diode. In another embodiment, the plurality light emitting elements is a different colored light emitting diode. The device further comprises a diffuser disposed above each light emitting element.

In one embodiment, the control panel is electrically coupled to the smart electronic glass and the plurality of light emitting elements. In one embodiment, a power supply is coupled to the control panel to supply power to the smart electronic glass, the plurality of light emitting elements. The control panel is configured to operate the light emitting elements and the smart electronic glass device. The smart electronic glass is configured to switch to an opaque state for the user to exercise on short-sightedness and switch to a transparent state for the user to exercise on farsightedness. This enables the user to view at different distance, comfortably up to 10 meters to 5+ miles away as the eye sight enhances & becomes more comfortable with increasing the distances. The device is configured to achieve both near & far without binocular/magnified lenses.

In one embodiment, the single open goggle chamber further comprises a rear portion contoured to receive a face contact surface of the user and a rubber seal is disposed at the rear portion to provide comfort to the user. In one embodiment, a head strap extends from the rear portion of the single open goggle chamber in order to allow the device to be worn on the head.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF DRAWINGS

The foregoing summary, as well as the following detailed description of the invention, is better understood when read in conjunction with the appended drawings. For the purpose of illustrating the invention, exemplary constructions of the invention are shown in the drawings. However, the invention is not limited to the specific methods and structures disclosed herein. The description of a method step or a structure referenced by a numeral in a drawing is applicable to the description of that method step or structure shown by that same numeral in any subsequent drawing herein.

DETAILED DESCRIPTION OF EMBODIMENTS

A description of embodiments of the present invention will now be given with reference to the Figures. It is expected that the present invention may be embodied in other specific forms without departing from its spirit or essential characteristics. The described embodiments are to be considered in all respects only as illustrative and not restrictive.

Figure 1:
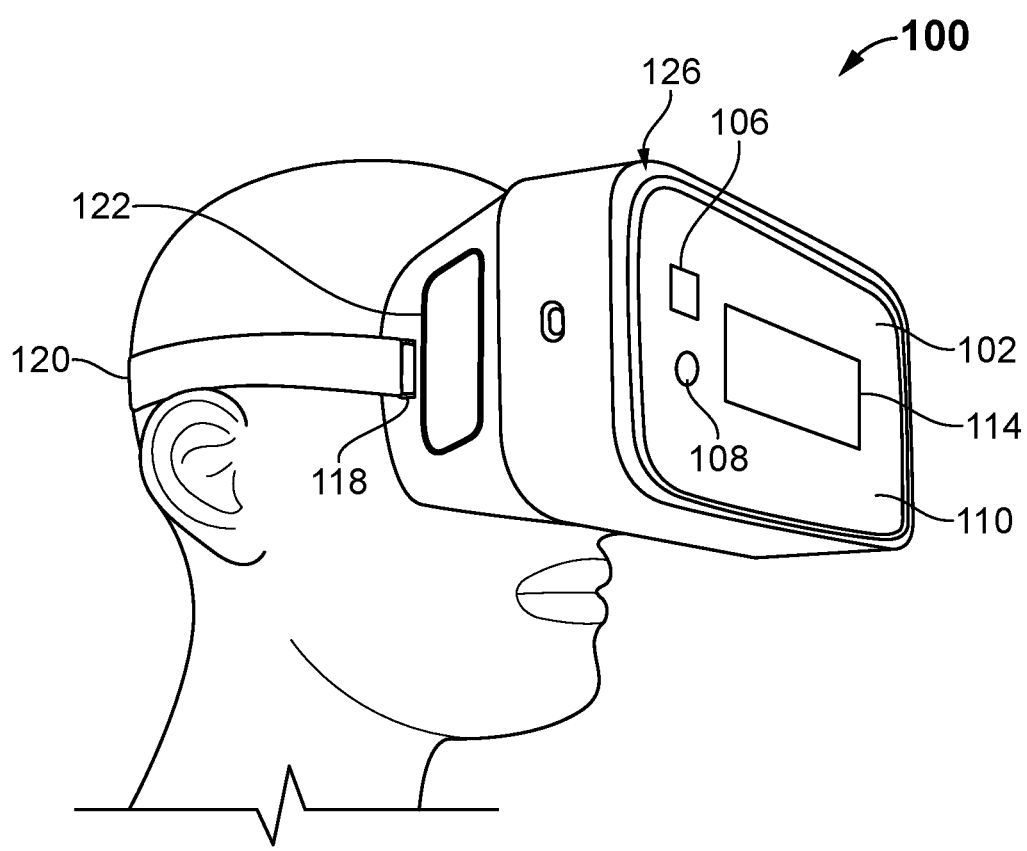
FIG. 1 exemplarily illustrates a user wearing an eye exercise device in an embodiment of the present invention.

Referring to FIG. 1-FIG. 8, an eye exercise device 100 comprising a single open goggle chamber 126 with no binocular or magnified lenses are illustrated. The present invention utilizes a smart electronic glass 116 in conjunction with a plurality of light emitting LED elements 124 to encourage ocular movements is illustrated. The eye exercise device 100 of the present invention is a portable device configured to provide ocular movements of various types, which includes, but not limited to, Up, down, left, right, right angle up, right angle down, left angle up, left angle down, far right up to far right down, far left up to far left down, bottom left top right up, bottom right down to top left up, right & left full circular directional eye movements. Referring to FIG. 1, the device 100 comprises a single open goggle chamber 126, a protective first plastic plate 110 that holds a protective screen 114, a second plastic plate 112, a plurality of light emitting LED elements 124, a control panel and a power supply. Referring to FIG. 1, the single open goggle chamber 126 including a front portion 102 and a rear portion 104 spaced apart from the front portion 102. The front portion 102 integral to the rear portion 104 forms a unitary body. The device 100 further comprises a strap 120 connected to an opposing lateral side 122 of the rear portion 104 of the frame 126.

Figure 2:
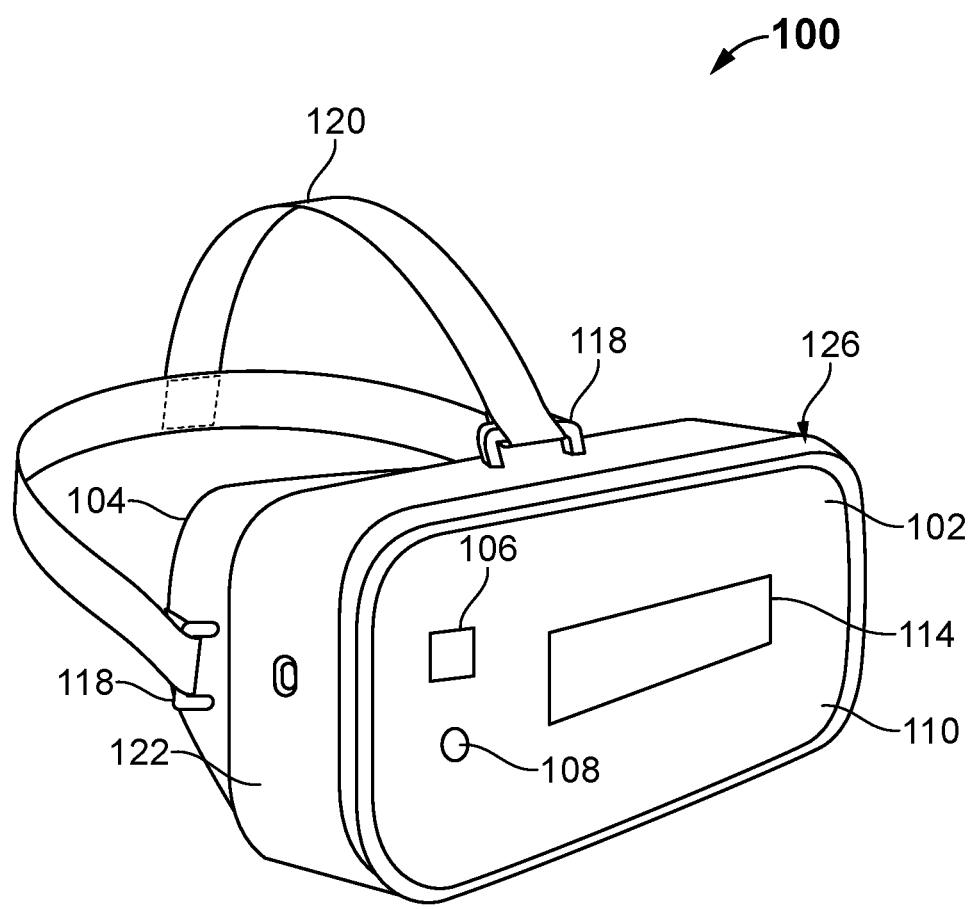
FIG. 2 exemplarily illustrates a perspective view of an eye exercise device in an embodiment of the present invention.

Referring to FIG. 2, the front protective first plate 110 that holds a protective screen 114, is provided at the front portion of the open goggle chamber 126. In one embodiment, the front protective first plate 110 comprises a transparent protective screen 114, which protects the components installed within the open goggle chamber 126 from dust or other similar particles. In one embodiment, the front protective first plate 110 further comprises an LCD display 106 and a power switch 108. The LCD display 106 is configured act as a user interface. The power switch 108 is configured to enable the user to turn on/off the device 100.

Figure 3:
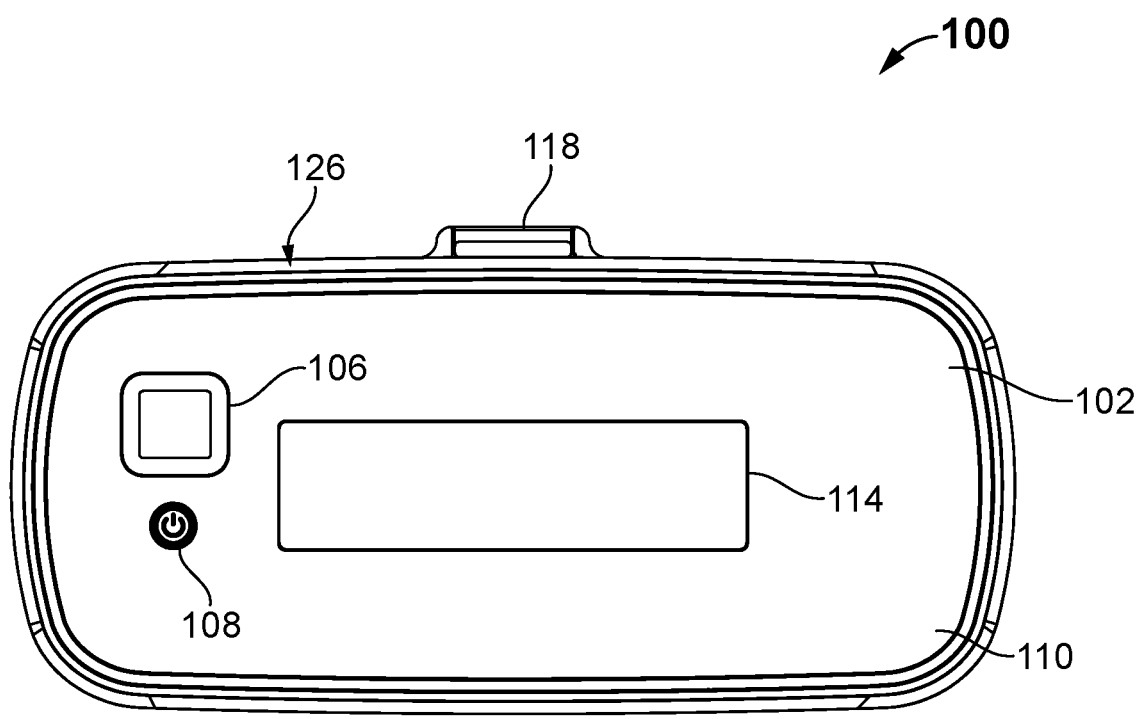
FIG. 3 exemplarily illustrates a front view of an eye exercise device in an embodiment of the present invention.
Figure 4:
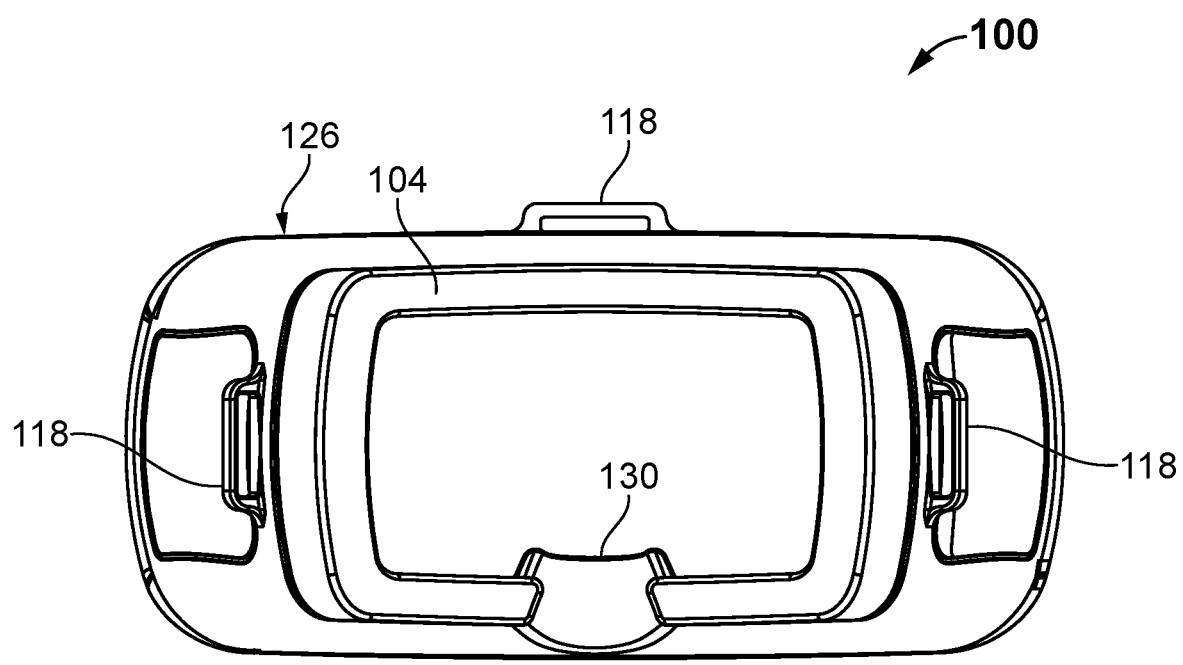
FIG. 4 exemplarily illustrates a rear view of an eye exercise device in another embodiment of the present invention.

Referring to FIG. 3, the front protective first plate 110 is disposed at the front portion 102. The front protective first plate 110 comprises a polycarbonate screen 114 disposed at a center region across an eye of a user. The front protective first plate 110 is provided for protecting the second plate 112 that holds all light emitting LED elements 124 and a smart electronic glass 116, from dust or the like. The device 100 further comprises a display 106 and power switch 108 in communication with the control panel. Referring to FIG. 4, the device 100 further comprises a rubber seal attached to the rear frame portion 104 of the single open goggle chamber 126 and configured to be interposed between the single open goggle chamber 126 and the wearer's face. The rear portion 104 contoured to receive a face contact surface of the user and the rubber seal is disposed at the rear portion 104 to provide comfort to the user. In an embodiment, the rear portion 104 comprises a nose bridge to comfortably place the device 100. In one embodiment, the nose bridge comprises a triangular structure. In some embodiments, the nose bridge comprises a C-shaped structure with a rubber seal for comfort 130.

Figure 5:
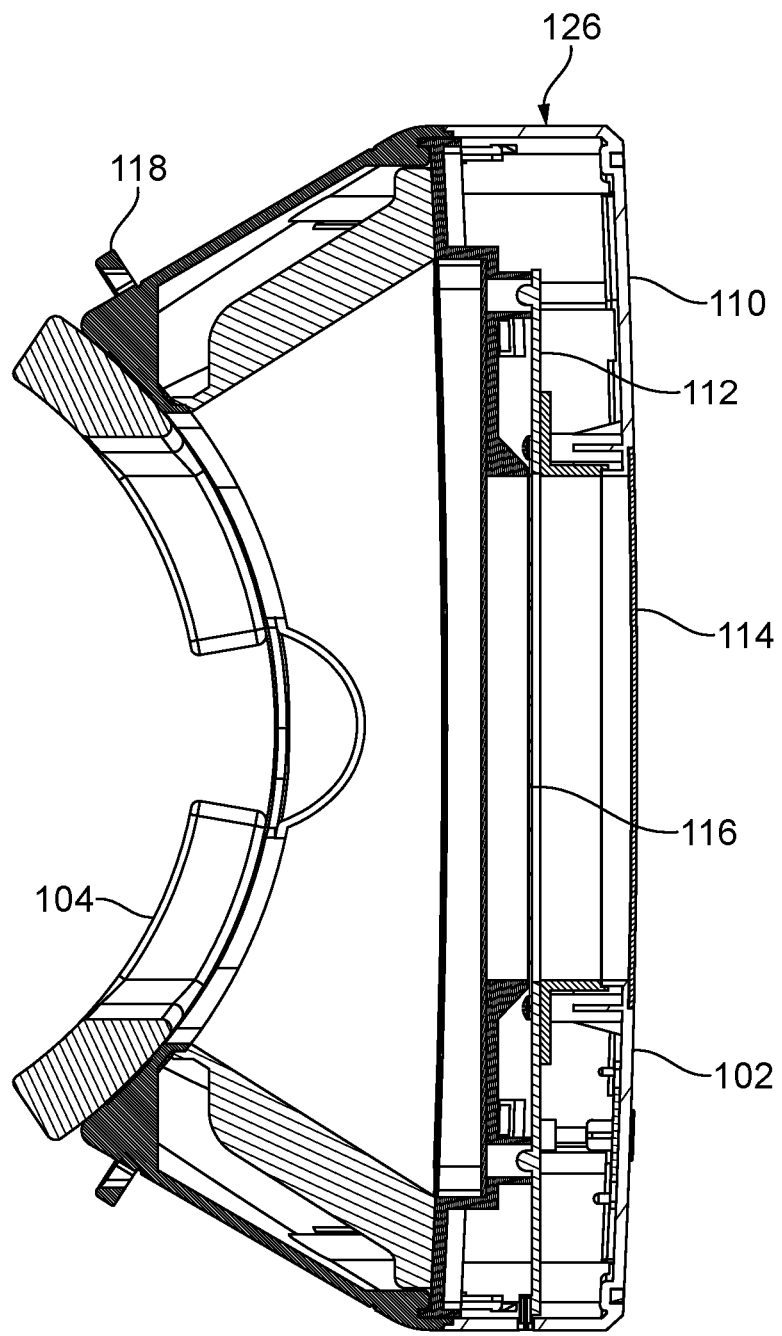
FIG. 5 exemplarily illustrates a cross-sectional view of an eye exercise device in an embodiment of the present invention.

Referring to FIG. 5, the second plate 112 that holds all light emitting LED elements 124 and a smart electronic glass 116 disposed behind the first plate 110 at the front portion 102 of the device 100. In another embodiment, the second plate 112 is disposed horizontally behind the first plate 110 of the front portion 102. The second plate 112 comprises a smart electronic glass 116 disposed at a center region. The smart electronic glass 116 and the polycarbonate protective screen 114 disposed in a substantially parallel relation to the user's forward line of sight. The smart electronic glass 116 is configured to switch to an opaque state for the user exercising for short-sightedness and switch to a transparent state for the user exercising for farsightedness.

Figure 6:
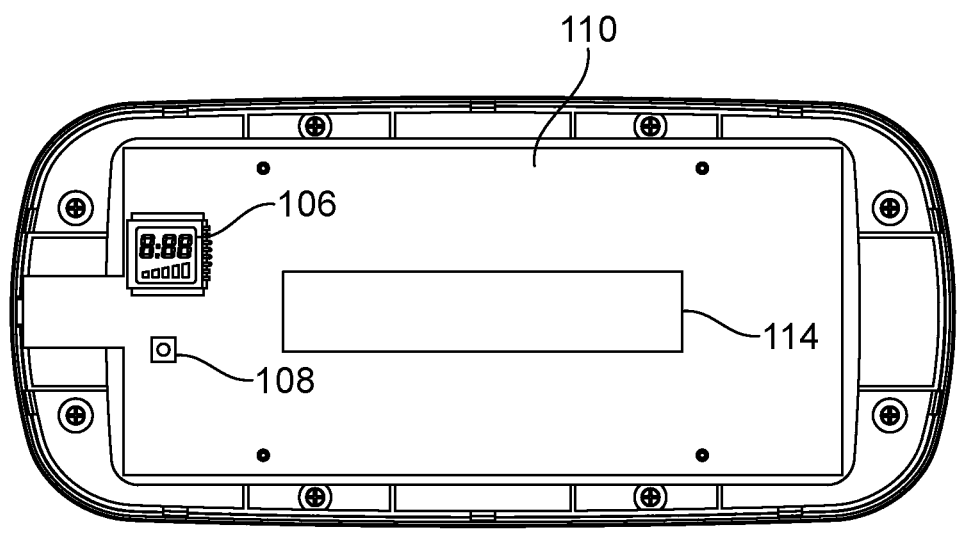
FIG. 6 exemplarily illustrates a protective first plate holding a protective polycarbonate screen, LCD display screen & the start/stop button of an eye exercise device in an embodiment of the present invention.
Figure 7:
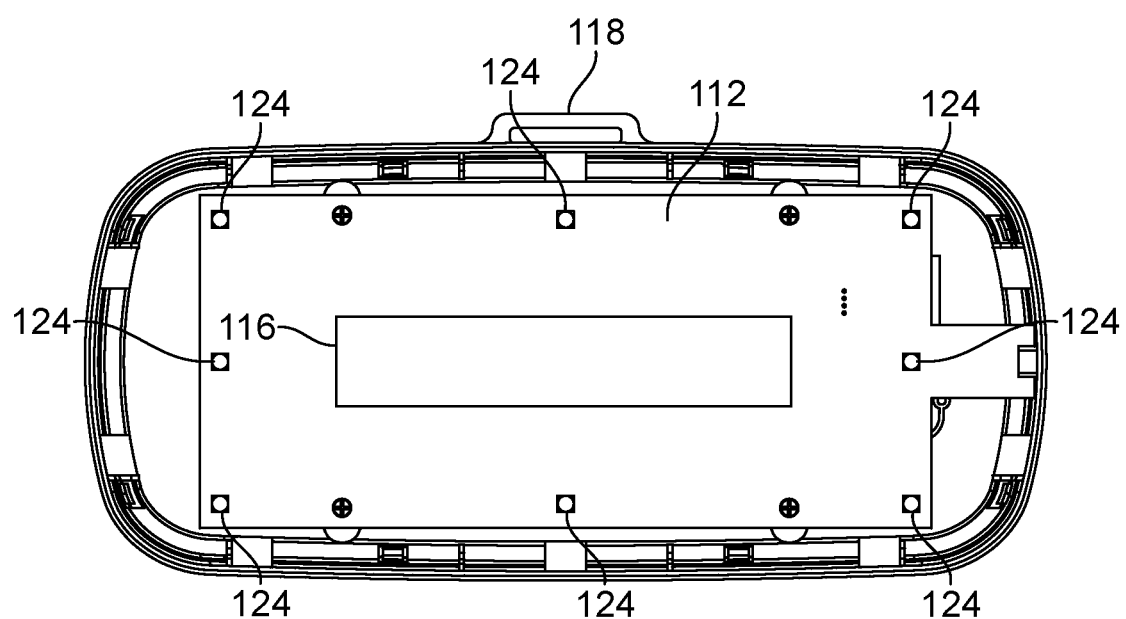
FIG. 7 exemplarily illustrates a second plastic plate comprising an electronic smart screen and the light emitting LED elements of the eye exercise device in an embodiment of the present invention.

Referring FIG. 6, the display 106 and power the switch 108 is disposed at a front portion 102 of the front protective first plate 110 that holds a protective screen 114, is illustrated. Referring to FIG. 7, the plurality of light emitting elements 124 are strategically arranged in the periphery of the second plate 112. In one embodiment, the light emitting elements 124 is a multi-colored LED. In another embodiment, the plurality of light emitting elements 124 comprises at least eight light emitting LEDs. In yet another embodiment, the plurality of light emitting elements 124 includes red, white, blue and green LEDs. In one example, position and color of the LEDs are as follows: first LED positioned at the top, white in color and second LED at top right, green in color and third LED at the right hand side, red in color and fourth LED at the bottom right, blue in color and fifth LED directly at the bottom, white in color and sixth LED at the bottom left hand side, green in color and seventh LED on the left hand side, red in color and the final eighth LED is positioned at the top left hand side, and blue in color.

Figure 8:
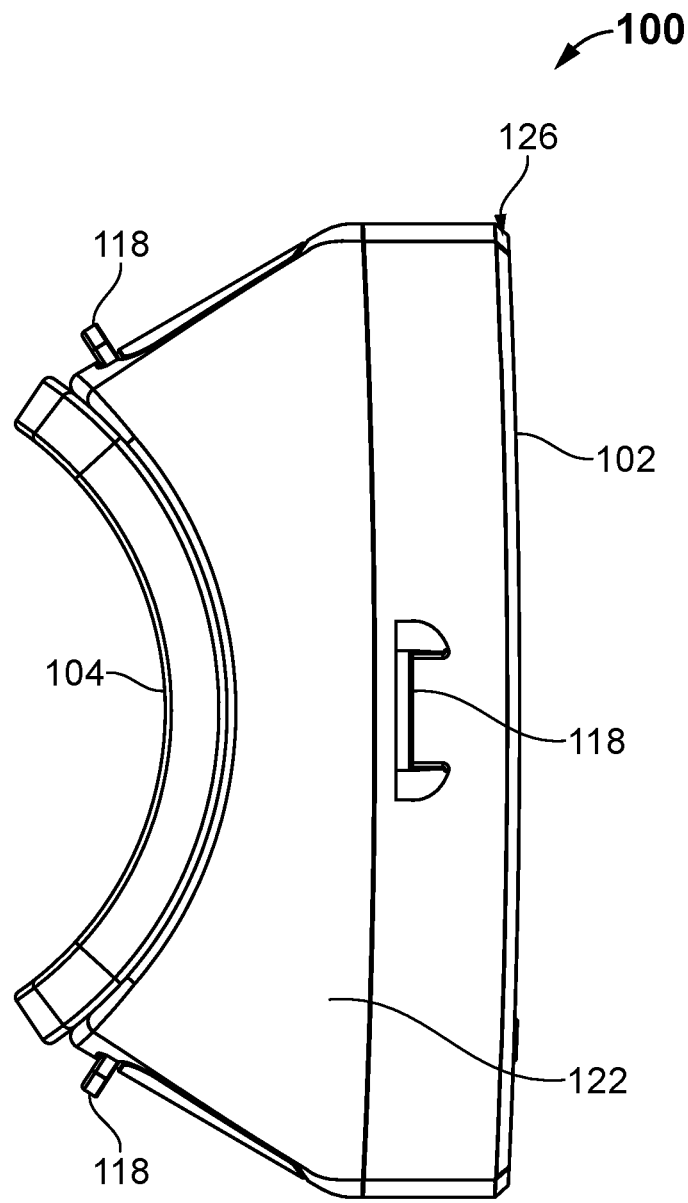
FIG. 8 exemplarily illustrates a top view of an eye exercise device in an embodiment of the present invention.

The control panel is electrically coupled to the smart electronic glass 116 and the plurality of light emitting elements 124. In one embodiment, the power supply is coupled to the control panel to supply power to the smart electronic glass 116 and the plurality of light emitting elements 124. In one embodiment, the power supply could be a rechargeable battery. A side view of an eye exercise device 100 is illustrated in FIG. 8. A provision 118 is provided to fasten the head strap 120 to the device 100. The head strap 120 wraps around the sides of user's face and head to keep the device 100 in position during exercise. In one embodiment, the head strap 120 is an adjustable head strap.

In another embodiment, the device 100 is supplied with components necessary to operate the device, including, but not limited to, processor, memory, hard drive size, operating system, audio, ports, battery, wireless unit, Bluetooth and charging port, PCB board, charging IC, resistance, step-up transformer. In another embodiment, the motherboard of the device 100 is a single side board. In one embodiment, LEDs are mounted in a predefined sequence on the motherboard and contacts of the LEDs are soldered. Further, the IC are installed on the motherboard by burn-in process after finishing the smart glass procedure. During operation of the device 100, the IC controls the LEDs, and the liquid crystal molecules aligns to allow light to pass through, providing a transparent state of smart glass 116. When the power is switched off the liquid crystal molecules are randomly oriented, thus scattering light and the smart glass 116 becomes opaque.

The control panel is configured to operate the multicolored LED lights in a numerical and multi rotational sequence and timing to engage the eyes and encourage specific ocular movements. These are specifically positioned at a distance from the face to achieve near sightedness and farsightedness exercises activation achieving optimal focus without binocular/magnified lenses. This is achieved using colored smart electronic glass at the front of the device 100 operating with the LED sequence providing a clear view for farsightedness and then switches to a dark/opaque glass for short sightedness exercise in an extended full-frontal device that captures both eyes in one single open goggle chamber without binocular/magnified lenses. In one embodiment, the smart electronic glass 116 is a liquid crystal privacy film, which responds to electric current. In another embodiment, the smart electronic glass 116 is made of electrochromic glass. The smart electronic glass 116 is capable of adjusting light transmission between transparent and opaque using AC power.

During operation of the device 100, when electrical supply is switched on, the liquid crystal molecules align, incident light passes through and the smart glass panel instantly becomes transparent & clear to visually see through. When the power is switched off the liquid crystal molecules are randomly oriented, thus scattering light and the smart electronic glass 116 becomes opaque. This enables any user whether near or far sighted to benefit from the exercises. Through regular use, the device 100 would assist with maintaining eye health and minimize the aging process for diminishing eye site & long screen use in today's society which is only becoming more intense.

In one embodiment, the LEDs/smart glass exercise sequence programmed in the device 100 is disclosed. Initially, the LEDs are turned on in sequence with total lighting time of 49 seconds and lighting interval of 1.5 seconds. Then, LEDs are turned on in either clockwise or anti clockwise sequence with total lighting time of 57 seconds and light interval of 1.5 seconds. At next step, all LEDs are turned off and the control panel turns on the power supply to the smart electronic glass, which allows the user to see outside the device with clear vision. At next step, the power supply to the smart electronic glass is turned off and the LED at the bottom of the smart electronic glass are turned on, so that user eye could rest, which is repeated for 25 seconds in total. In Total, the exercise sequence is programmed for 5 minutes.

Advantageously, the present invention provides the eye exercise device 100 in the single open goggle chamber 126 without binocular/magnified lenses. Unlike existing device 100, the present invention is positioned at a certain distance from the face that creates blurriness/focus naturally with no binocular or magnified lenses in one singular open chamber, which strengthens the expansion ability of the extra ocular muscles & contributes to overcoming eye muscle fatigue caused by having your eyes fixated on near objects for a long period of time. The device 100 is configured to encourage a full stretching of both eyes to cross over the nose to the far right and far left at a certain distance from the face without any optical or binocular lenses. The device 100 provides at least three separate sequences that are stitched together in a specific numerical order that runs just under 5 minutes for a complete eye exercise program and caters for computer vision syndrome (CVS).

The device 100 provides an affordable solution for a general person in the comfort of their own home. The present invention naturally works on near sightedness or farsightedness. The device 100 provides all three steps of exercises in one complete portable device, which includes circular motion, crisscross motion, nearsightedness & farsightedness motion. The device 100 provides a compact unit that fits easily and comfortably to the head and encompasses a series of eye exercises that aide's in the recovery of "eye strain" and other ailments such as tired eyes and dry eyes. The exercise also caters for near sightedness and far sightedness without the aid of binocular lenses or ocular lenses which is critical. The device 100 enables the user to simply follow a set programmed LED lights that exercise their eyes and encourages more ocular movements to rejuvenate the eye and eye muscles providing instant & long-term relief to the user.

Preferred embodiments of this invention are described herein, including the best mode known to the inventors for carrying out the invention. It should be understood that the illustrated embodiments are exemplary only, and should not be taken as limiting the scope of the invention.

The foregoing description comprise illustrative embodiments of the present invention. Having thus described exemplary embodiments of the present invention, it should be noted by those skilled in the art that the disclosures are exemplary only, and that various other alternatives, adaptations, and modifications may be made within the scope of the present invention. Merely listing or numbering the steps of a method in a certain order does not constitute any limitation on the order of the steps of that method. Many modifications and other embodiments of the invention will come to mind to one skilled in the art to which this invention pertains having the benefit of the teachings presented in the foregoing descriptions. Although specific terms may be employed herein, they are used only in generic and descriptive sense and not for purposes of limitation. Accordingly, the present invention is not limited to the specific embodiments illustrated herein.

What is claimed is:

1. An eye exercise device, comprising:
   a single open goggle chamber having a front portion;
   a protective first plate comprising a protective screen disposed at the front portion of a goggle frame;
   a second plate disposed behind the first plate at the front portion, wherein the second plate comprises a smart electronic glass disposed at a center region across an eye of a user;
   a plurality of light emitting elements arranged in the periphery of the second plate;
   a control panel electrically coupled to the smart electronic glass and the plurality of light emitting elements, and
   a power supply coupled to the control panel to supply power to the smart electronic glass and the plurality of light emitting elements,
   wherein the smart electronic glass is configured to switch to an opaque state for the user exercising short sightedness,
   wherein the smart electronic glass is configured to switch to a transparent state for the user exercising farsightedness, and
   wherein the plurality of light emitting elements is configured to emit light in a predefined sequence, thereby encouraging specific ocular stretching movements to rejuvenate the eye and eye muscles to provide instant relief to the user.

2. The eye exercise device of claim 1, wherein the protective screen is a polycarbonate protective screen, disposed at a center region across an eye of a user.

3. The eye exercise device of claim 1, further comprises a diffuser disposed above each of said plurality of light emitting elements.

4. The eye exercise device of claim 1, wherein the goggle frame comprises a rear portion contoured to receive a face contact surface of the user and a rubber seal is disposed at the rear portion to provide comfort to the user.

5. The eye exercise device of claim 1, further comprising a head strap that extends from a rear portion of the single open goggle chamber.

6. The eye exercise device of claim 1, further comprises one or more electronic components coupled to the control panel.

7. The eye exercise device of claim 1, wherein the light emitting element is a light emitting diode.

8. The eye exercise device of claim 1, wherein the plurality of light emitting elements comprises different color light emitting diodes.

* * * * *